(12) United States Patent
Nielsen et al.

(10) Patent No.: US 9,852,717 B2
(45) Date of Patent: Dec. 26, 2017

(54) ULTRASOUND IMAGE THREE-DIMENSIONAL (3D) PICTOGRAM

(71) Applicant: B-K MEDICAL APS, Herlev (DK)

(72) Inventors: Torben Svanberg Nielsen, Copenhagen (DK); Kaj Dunkan, Stenlille (DK); Jesper Helleso Hansen, Kobenhavn NV (DK); John Antol, Nahant, MA (US); Michael Leismann, Hvidovre (DK)

(73) Assignee: B-K Medical Aps, Herlev (DK)

( * ) Notice: Subject to any disclaimer, the term of this patent is extended or adjusted under 35 U.S.C. 154(b) by 629 days.

(21) Appl. No.: 14/250,450

(22) Filed: Apr. 11, 2014

(65) Prior Publication Data

US 2015/0294495 A1    Oct. 15, 2015

(51) Int. Cl.
  *G06T 19/20* (2011.01)
  *G09G 5/377* (2006.01)
  *A61B 8/00* (2006.01)
(52) U.S. Cl.
  CPC .............. *G09G 5/377* (2013.01); *A61B 8/468* (2013.01); *G06T 2200/04* (2013.01); *G06T 2207/10136* (2013.01); *G06T 2207/20221* (2013.01); *G06T 2207/30004* (2013.01)

(58) Field of Classification Search
  None
  See application file for complete search history.

(56) References Cited

U.S. PATENT DOCUMENTS

2004/0122310 A1\* 6/2004 Lim .................. A61B 8/00
                                                                   600/426

\* cited by examiner

*Primary Examiner* — Said Broome
(74) *Attorney, Agent, or Firm* — Anthony M. Del Zoppo, III; Driggs, Hogg, Daugherty & Del Zoppo, Co., LPA

(57) ABSTRACT

An ultrasound imaging system includes a transducer array with at least one transducer element. The system further includes an echo processor that processes ultrasound echo signals received by at least one transducer element, producing an image of scanned tissue of interest. The system further includes memory that stores a plurality of 3D pictogram, each representing different anatomical regions of a subject. The system further includes a pictogram processor that identifies a 3D pictogram of the plurality of 3D pictogram corresponding to the scanned tissue of interest. The 3D pictogram includes a 3D pictorial representation of an anatomical region including the scanned tissue of interest. The system further includes a display monitor. The system further includes a rendering engine that displays the image and the 3D pictogram via the display monitor. The 3D pictogram is overlaid over a pictogram region of the displayed image.

15 Claims, 6 Drawing Sheets

ULTRASOUND IMAGE THREE-DIMENSIONAL (3D) PICTOGRAM

TECHNICAL FIELD

The following generally relates to ultrasound imaging and more particularly to a three-dimensional (3D) pictogram (body mark) overlaid over an ultrasound image of a sub-portion an anatomy of a subject and pictorially representing the anatomy.

BACKGROUND

Ultrasound (US) imaging provides useful information about the interior characteristics (e.g., anatomical tissue, material flow, etc.) of a subject under examination. An ultrasound imaging system has included a probe with an ultrasound transducer array, a console, a display, and a keyboard. The transducer array transmits an ultrasound signal into a field of view and receives echoes produced in response to the signal interacting with structure therein. The console controls transmission and reception. The echoes are processed by the console, which generates one or more images indicative of the structure that are visually presented in the display region.

FIG. 1 shows an example image 102 of a sub-portion of a breast of a subject. In particular, the image 102 shows a sub-portion of the breast that includes a mass 104. However, from FIG. 1, the reading clinician would not be apprised of the location within the breast, nor which breast, simply from the image 102. As such, such images have been labeled with a body-marker. For example, the image 102 includes the body-marker 106, which identifies the breast as the left breast by virtue of the shape of the marker 106, with a right end 108 representing a side adjacent the sternum and a left end 110 representing an opposing side adjacent to the shoulder/upper arm. The body-marker 106 further shows a nipple 112 and an areola 114. The illustrated body-marker 106 further includes indicia 116 that shows a location and an orientation of the transducer array.

As illustrated, generally, body-markers such as the body marker 106 attempt to depict a region at or near the scanned region of the body. In general, the user, after generation of the image, views a text based list of available body-marker. The user then selects a body-marker from the list that bests represents the scanned region of the body, and the selected body-marker is overlaid over the image 102. The user then places the graphical indicia 116 with respect to the body marker 102 to provide the clinician with a graphic that shows the approximate location and orientation of the transducer array during data acquisition.

Unfortunately, the body-marker 106 is a two-dimensional (2D) cartoonish like graphic, whereas the actual scanned anatomy is three dimensional. As such, the body-marker 106 does not well-reflect the actual scanned tissue (the mass 104 in the image 102), and the graphical indicia 116 does not well reflect the actual location and orientation of the transducer array during data acquisition.

SUMMARY

Aspects of the application address the above matters, and others.

In one aspect, an ultrasound imaging system includes a transducer array with at least one transducer element. The system further includes an echo processor that processes ultrasound echo signals received by at least one transducer element, producing an image of scanned tissue of interest. The system further includes memory that stores a plurality of 3D pictograms, each representing different anatomical regions of a subject. The system further includes a pictogram processor that identifies a 3D pictogram of the plurality of 3D pictogram corresponding to the scanned tissue of interest. The 3D pictogram includes a 3D pictorial representation of an anatomical region including the scanned tissue of interest. The system further includes a display monitor. The system further includes a rendering engine that displays the image and the 3D pictogram via the display monitor. The 3D pictogram is overlaid over a pictogram region of the displayed image.

In another aspect, a method includes superimposing a 3D body mark over a 3D body mark region of a display region, wherein the display region concurrently displays an ultrasound image of scanned tissue of interest in an image display region of the display region, and wherein the 3D body mark includes a region of the body including the scanned tissue of interest.

In another aspect, a computer readable storage medium is encoded with computer readable instructions. The computer readable instructions, when executed by a processer, causes the processor to: transmit an ultrasound signal into a field of view, receive an echo signal generated in response to the ultrasound signal interacting with structure in the field of view, process the echo signal, generating an ultrasound image, display the ultrasound image of the structure, identify a 3D pictogram pictorially representing the structure in the image, and superimpose the 3D pictogram over the ultrasound image.

Those skilled in the art will recognize still other aspects of the present application upon reading and understanding the attached description.

BRIEF DESCRIPTION OF THE DRAWINGS

The application is illustrated by way of example and not limitation in the figures of the accompanying drawings, in which like references indicate similar elements and in which.

DETAILED DESCRIPTION

Figure 1:
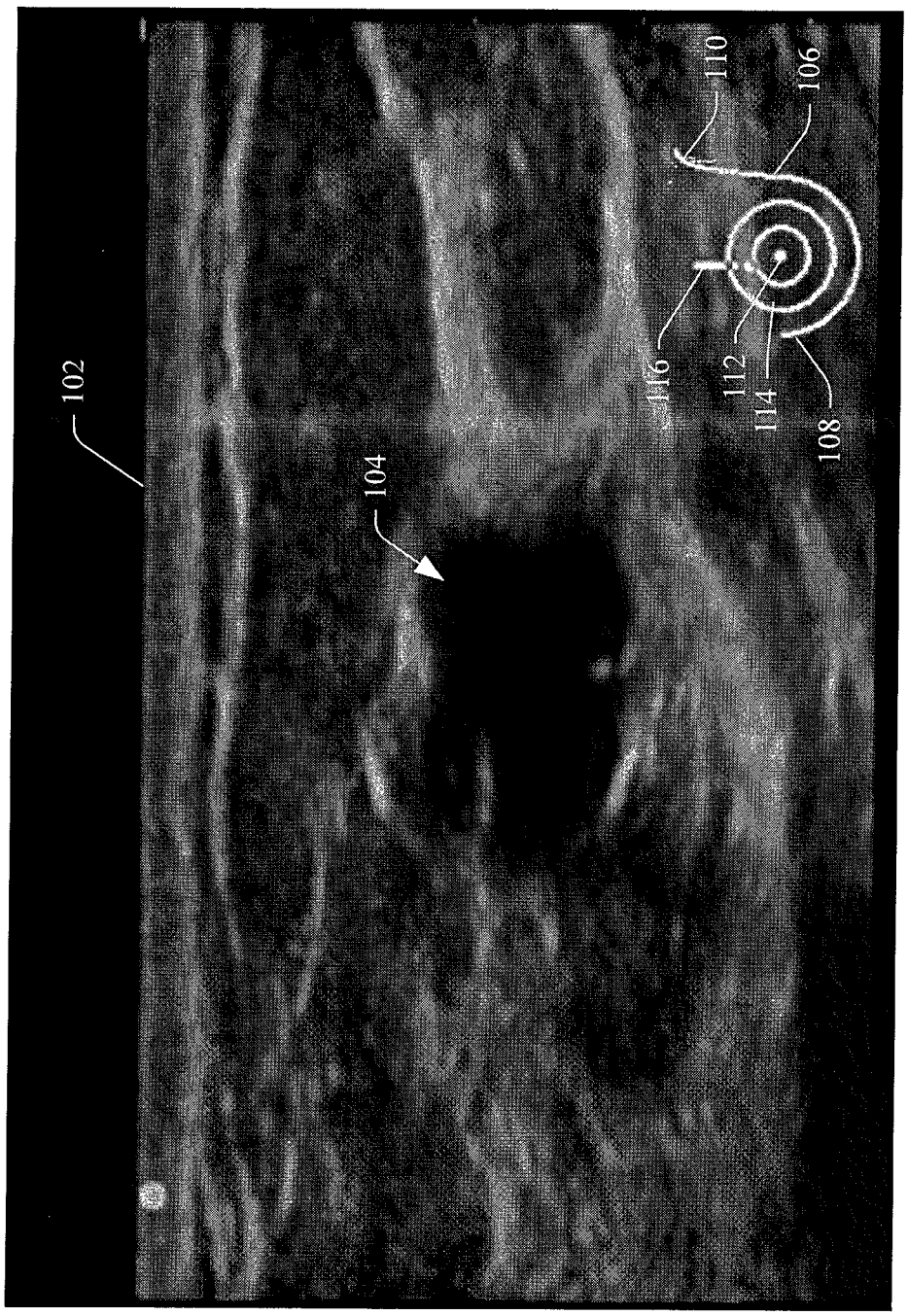
FIG. 1 shows an ultrasound image with a prior art body-marker superimposed there over.
Figure 2:
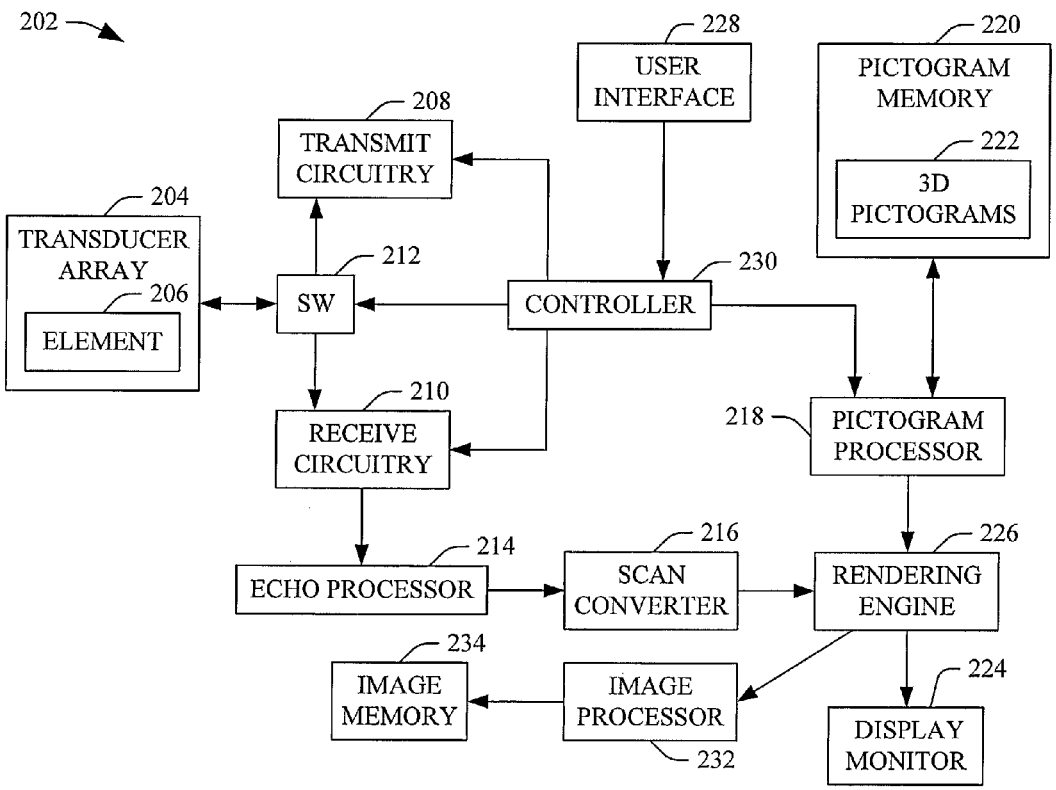
FIG. 2 schematically illustrates an example imaging system including a pictogram processor that facilitates selecting and rendering a 3D pictogram for a displayed image.

FIG. 2 schematically illustrates an ultrasound (US) imaging system 202. The ultrasound imaging system 202 includes a one-dimensional (1D) or two-dimensional (2D) transducer array 204 with at least one transducer element 206. At least one transducer element 206 is configured to transmit ultrasound signals and receive echo signals. Suitable array configurations include, but are not limited to, linear, curved (e.g., concave, convex, etc.), circular, etc., full populated or sparse, etc.

The ultrasound imaging system 202 further includes transmit circuitry 208 that selectively excites one or more of at least one transducer element 206. More particularly, the transmit circuitry 208 generates a set of pulses (or a pulsed signal) that are conveyed to the transducer array 204. The set of pulses excites at least one transducer circuitry 208, causing at least one transducer element 206 to transmit an ultrasound signal into an examination scan field of view.

The ultrasound imaging system 202 further includes receive circuitry 210 that receives a set of echoes (or echo signals) generated in response to the transmitted ultrasound signals. The echoes, generally, are a result of the interaction between the emitted ultrasound signals and the object (e.g., flowing blood cells, organ cells, etc.) in the scan field of view. The receive circuit 210 may be configured for spatial compounding, filtering (e.g., FIR and/or IIR), and/or other echo processing.

The ultrasound imaging system 202 further includes a switch (SW) 212. In the illustrated embodiment, the transmit signal and the receive signal are routed through the switch 212. In general, the switch 212 electrically connects the transmit circuitry 208 and the transducer array 204 during transmit operations, and the switch 212 electrically connects the receive circuitry 210 and the transducer array 204 during receive operations.

The ultrasound imaging system 202 further includes an echo processor (e.g., a beamformer) 214 that processes the received echoes. For example, in B-mode, this may include applying time delays and weights to the echoes and summing the delayed and weighted echoes, and generating an image. The ultrasound imaging system 202 further includes a scan converter 216 that scan converts the processed data for display, e.g., by converting the beamformed data to the coordinate system of a display monitor used to visually present the processed data.

The ultrasound imaging system 202 further includes a pictogram processor 218 and pictogram memory 220, which stores 3D pictograms 222. As described in greater detail below, the pictogram processor 218 facilitates selection of an appropriate 3D pictogram, for example, from the pictogram memory 220, for inclusion with a displayed image. This may include allowing manipulation (e.g., pan, rotate, pivot, zoom, layer, etc.) of a selected 3D pictogram to place graphical indicia representing a location and/or orientation of the transducer array during data acquisition. The resulting image includes a 3D pictogram that well-reflects the actual scanned tissue and/or graphical indicia that well-reflects the actual location and orientation of the transducer array 204 during data acquisition.

The pictogram processor 218 can be implemented via a processor (e.g., a central processing unit (CPU), a microprocessor (μCPU), a graphical processing unit (GPU), or the like) executing computer instructions encoded or stored on computer readable storage medium, which excludes transitory medium and includes physical memory and/or other non-transitory storage medium. Additionally or alternatively, the processor can execute computer instructions carried in a signal, by a carrier wave, or other transitory medium to implement the pictogram processor 218.

The ultrasound imaging system 202 further includes a display monitor 224. The display monitor 224 can be a cathode ray tube (CRT), a liquid crystal display (LCD), a light emitting diode (LED), and/or other display monitor. The display monitor 224 includes a display region, which can visually present images. The ultrasound imaging system 202 further includes a rendering engine 226. The rendering engine 226 renders images and/or pictograms via the display monitor 224. In one instance, this includes superimposing a pictogram over a visually displayed image, for example, in a pictogram display region of the image.

The ultrasound imaging system 202 further includes a user interface 228. The user interface 228 includes include one or more input devices (e.g., a button, a knob, a slider, a touch pad, a touch screen, etc.) and/or one or more output devices (e.g., a display screen, a touch screen, lights, a speaker, etc.). The user interface 228 a user to select and/or manipulate a pictogram for display on an image. The ultrasound imaging system 202 further includes a controller 230 (e.g., a microprocessor, a central processing unit (CPU), etc.). The controller 230 controls one or more of the components of the system 202, such as at least the transmit circuitry 208, the receive circuitry 210, the switch 212, and the pictogram processor 218.

The ultrasound imaging system 202 further includes an image processor 232. The image processor 232 at least associates a displayed image from the scan converter 216 with a 3D pictogram selected for the image from the 3D pictograms 222. This may include including the 3D pictogram in the electronic file of the image, including the 3D pictogram in a separate file and linking the files, and/or other approach so that when the image is displayed the 3D pictogram is displayed concurrently therewith. Image memory 234 store the output of the image processor 232. The image memory 234 can be local to the ultrasound system 202 and/or remote therefrom.

In one instance, the transducer array 204 is part of a probe and the transmit circuitry 208, the receive circuitry 210, the switch 212, the echo processor 214, the scan converter 216, the pictogram processor 218, the pictogram memory 220, the 3D pictograms 222, the display monitor 224, the rendering engine 226, the user interface 228, and controller 230 are part of a console. Communication there between can be through a wired (e.g., a cable and electro-mechanical interfaces) and/or wireless communication channel. In this instance, the console can be similar to a portable computer such as a laptop, a notebook, etc., with additional hardware and/or software for ultrasound imaging.

Alternatively, the console can be part (fixed or removable) of a mobile or portable cart system with wheels, casters, rollers, or the like, which can be moved around. In this instance, the display 224 may be separate from the console and connected thereto through a wired and/or wireless communication channel. Where the cart includes a docking interface, the laptop or notebook computer type console can be interfaced with the cart and used. An example of a cart system where the console can be selectively installed and removed is described in US publication 2011/0118562 A1, entitled "Portable ultrasound scanner," and filed on Nov. 17, 2009, which is incorporated herein in its entirety by reference.

Alternatively, the components (i.e., 204-230) are all housed and enclosed within a hand-held ultrasound apparatus, with a housing that mechanically supports and/or shields the components within. In this instance, the transducer array 204, the user interface 228, and/or the display 224 are part of the housing, being structurally integrated or part of a surface or end of the hand-held ultrasound apparatus. An example of a hand-held device is described in U.S. Pat. No. 7,699,776, entitled "Intuitive Ultrasonic Imaging System and Related Method Thereof," and filed on Mar. 6, 2003, which is incorporated herein in its entirety by reference.

Figure 3:
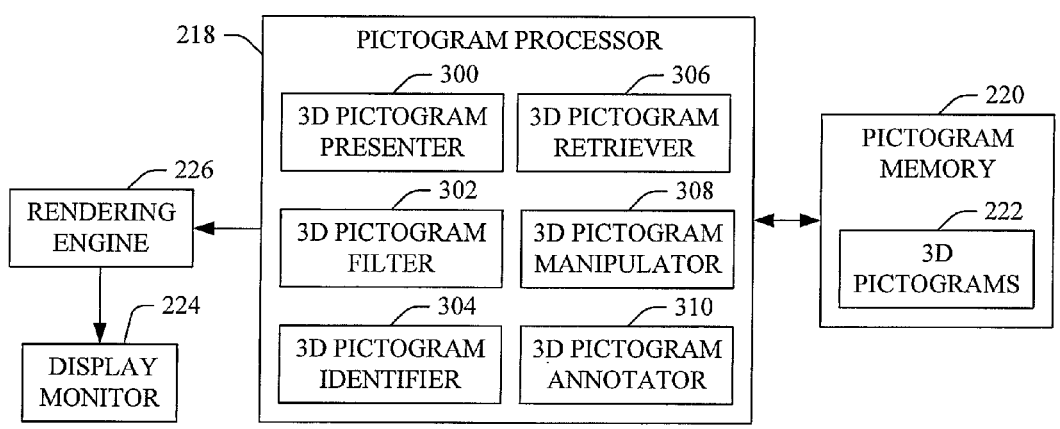
FIG. 3 schematically illustrates an example of the pictogram processor of FIG. 2.

FIG. 3 schematically illustrates an example of the pictogram processor 218 in connection with the pictogram memory 220, the rendering engine 226, and the display monitor 224.

In one instance, the pictogram processor 218 is invoked in response to a signal from the user interface 228 indicative of a user request for a pictogram. In another instance, displaying an image via the display monitor 224 automatically invokes pictogram processor 218. In other embodiments, the pictogram processor 218 is otherwise invoked.

The pictogram processor 218 includes a 3D pictogram presenter 300. The 3D pictogram presenter 300, in response to the pictogram processor 218 being invoked, transmits a signal to the rendering engine 226. The signal indicates the available pictograms in the pictogram memory 220, or the 3D pictograms 222. In one instance, the signal includes graphics such as thumb nails or other pictures that pictorially show what the 3D pictograms look like.

In another instance, the signal includes textual indicia describing each 3D pictogram. The textual indicia can include the name of the electronically formatted file of the 3D pictogram and/or other textual indicia. In yet another instance, the signal includes a combination of the pictorial and textual indicia, and/or at least one of the pictorial or textual indicia and other indicia. In any instance, the rendering engine 226 visually presents available 3D pictograms via the display monitor 224.

The pictogram processor 218 further includes a 3D pictogram filter 302 that filters the 3D pictograms 222 prior to the 3D pictogram presenter 300 transmitting the signal. In one instance, the 3D pictogram filter 302 passes only a sub-set of the available 3D pictograms. For example, where the displayed image is a breast image, the 3D pictogram filter 302 may only pass 3D pictograms related to the breast. The pictogram processor 218 can be apprised of this information from the controller 230, a user input, the image file, and/or otherwise. In another instance, the 3D pictogram filter 302 is omitted.

The pictogram processor 218 further includes a 3D pictogram identifier 304. The 3D pictogram identifier 304 receives a signal from the user interface 228 (through the controller 230) that identifies the 3D pictogram of interest to the user. The user can select a particular 3D pictogram of interest via an input device such as a mouse, a keyboard, a touch screen, etc. The pictogram processor 218 further includes a 3D pictogram retriever 306 that the identified 3D pictogram from the pictogram memory 220, and provides the retrieved 3D pictogram to the rendering engine 226, which displays the retrieved 3D pictogram.

The pictogram processor 218 further includes a 3D pictogram manipulator 308. The 3D pictogram manipulator 308 provides a set of tools which allow a user to manipulate the retrieved and displayed 3D pictogram. Such manipulation may include, but is not limited to, one or more of panning, rotating, pivoting, zooming, layering, etc. the displayed 3D pictogram. In one instance, this allows a user to spatially orient the displayed 3D pictogram on the image so that scanned and/or other tissue of interest is visible to a human observer of the image.

In another instance, the manipulation of the 3D pictogram allows a user to apply different levels of anatomical layers (e.g., skin only, organ only, muscle only, vein only, a combination thereof, etc.) to the 3D pictogram. Such anatomical layers allow for visually emphasizing particular tissue, removing particular tissue (e.g., tissue visually obscuring tissue of interest), showing particular tissue as an anatomical frame of reference, etc. The 3D pictogram may include a sub-portion of the body or the entire body. With the later, the manipulation may include a reduction of the entire body.

The pictogram processor 218 further includes a 3D pictogram annotator 310. The 3D pictogram annotator 310 provides a set of tools which allow a user to place graphical indicia representing the transducer array 204 with respect to the tissue illustrated in the displayed pictogram. The graphical indicia, one instance, can be placed to show a location of the transducer array 204 with respect to the scanned tissue. In another instance, the graphical indicia shows a spatial orientation of the transducer array 204 with respect to the tissue. In yet another instance, the graphical indicia shows both and/or other information.

Figure 4:
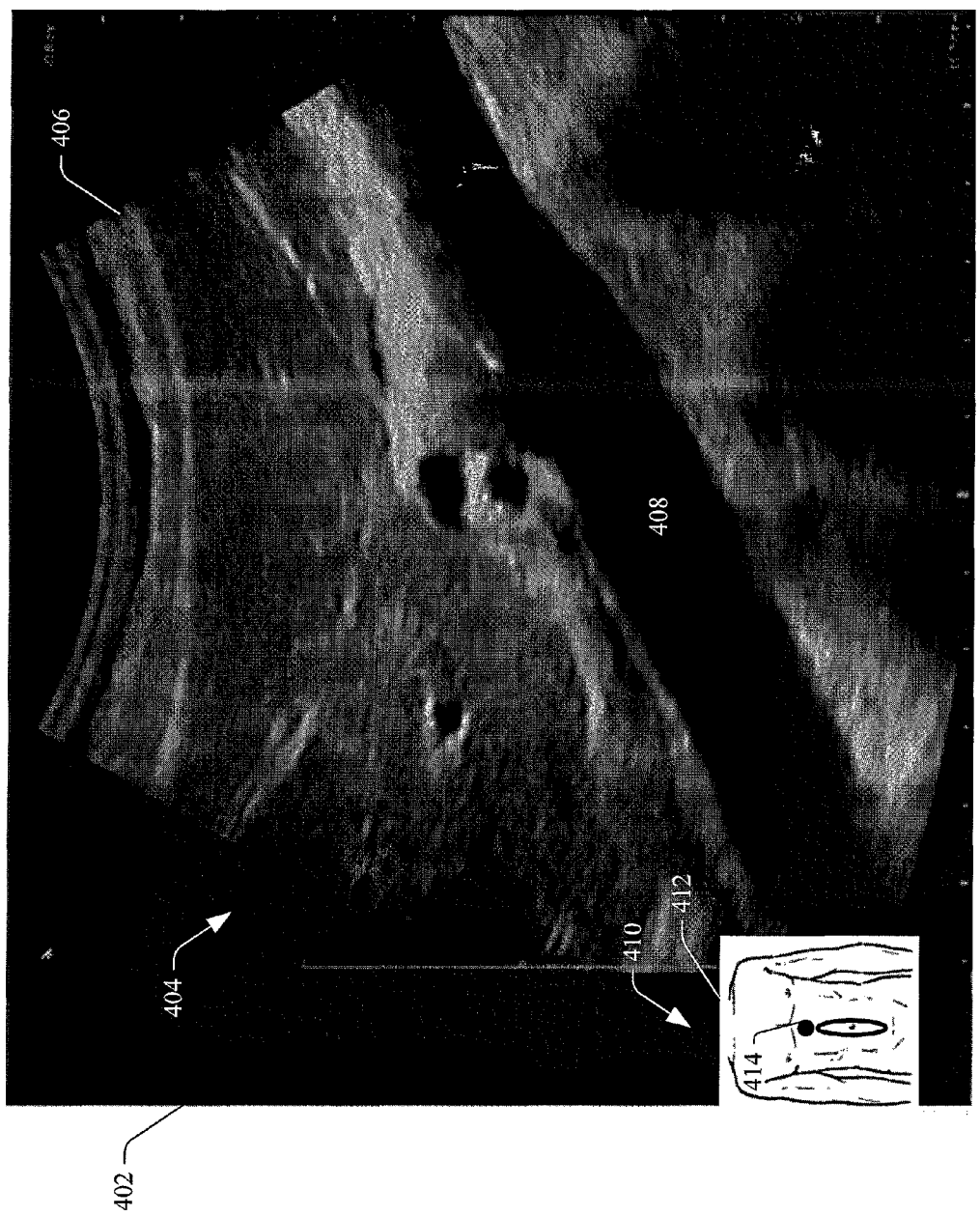
FIG. 4 shows an image of the abdominal aorta and a pictogram of a human body from the waist to the neck with graphical indicia showing a location and orientation of the transducer array during data acquisition of the image.
Figure 5:
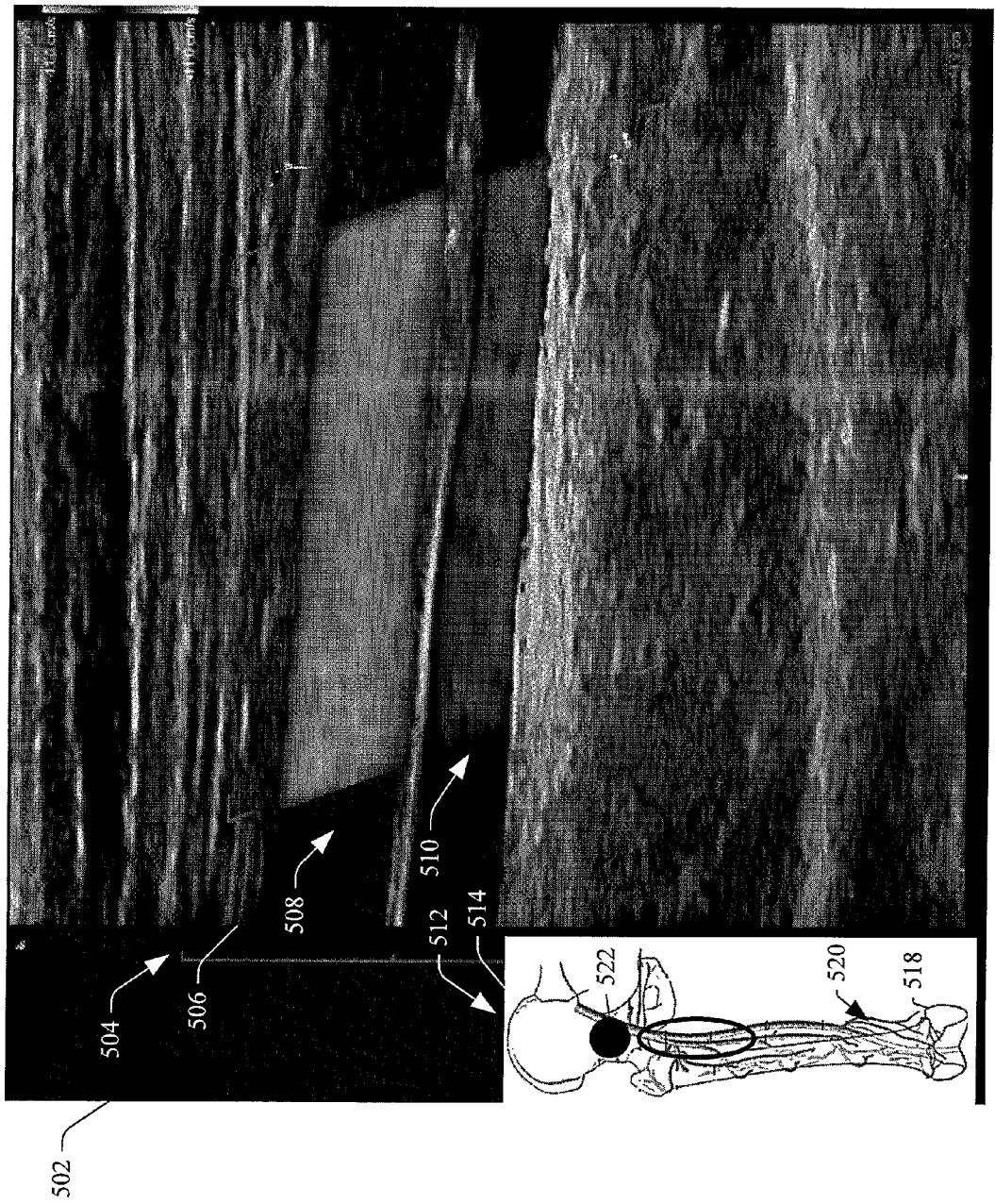
FIG. 5 shows an image of the femoral vein and artery and a pictogram of the pelvis region and one leg, showing only layers of bone and vessel, with graphical indicia showing a location and orientation of the transducer array during data acquisition of the image.
Figure 6:
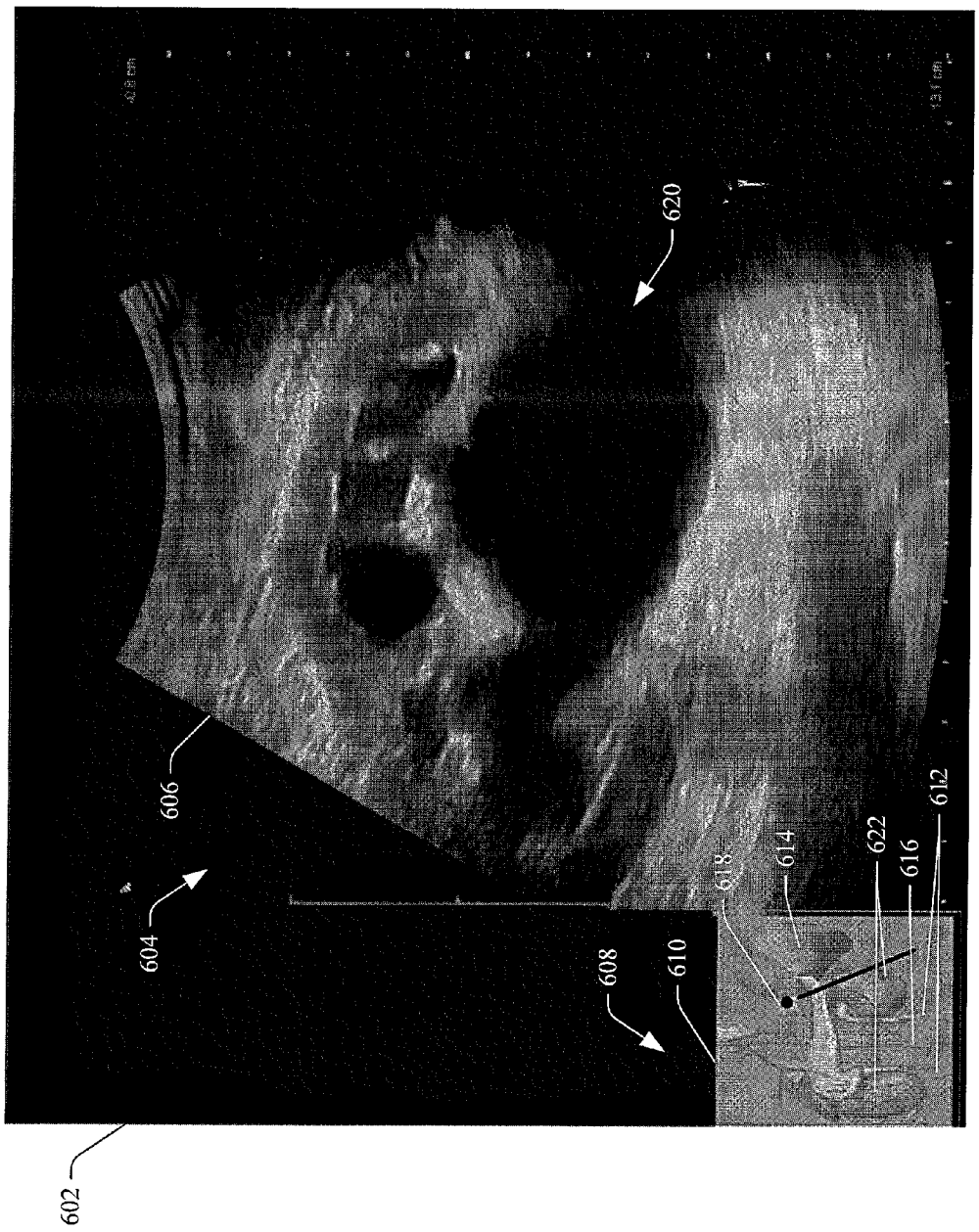
FIG. 6 shows an image of the renal pelvis calyces and a pictogram of the kidneys, ureters, etc., showing only layers of certain organs and vessel, with graphical indicia showing a location and orientation of the transducer array during data acquisition of the image.

FIGS. 4, 5, and 6 show example 3D pictograms in connection with displayed images.

In FIG. 4, a display region 402 includes an image display region 404 that visually presents an image 406 with pixels intensities representing a scanned abdominal aorta 408. The image 406, in this example, was acquired using a 4.3 MHz frequency and tissue harmonic imaging, in which a deep penetrating fundamental frequency is emitted into the body and a harmonic overtone is detected.

The display region 402 further includes pictogram display region 410. In the illustrated embodiment, a 3D pictogram 412 is visually presented in the pictogram display region 410. The 3D pictogram 412 includes a 3D representation of a human body from the waist to the neck, showing only layers of skin. Graphical indicia 414 shows a location and orientation of the transducer array during data acquisition.

In FIG. 5, a display region 502 includes an image display region 504 that visually presents an image 506 with pixels intensities representing a scanned femoral artery 508 and vein 510 using color Doppler. The display region 502 further includes pictogram display region 512. In the illustrated embodiment, a 3D pictogram 514 is visually presented in the pictogram display region 512. The 3D pictogram 514 includes a 3D representation of a pelvis and one leg, showing only layers of bone 518 and vessel 520. Graphical indicia 522 shows a location and orientation of the transducer array during data acquisition.

In FIG. 6, a display region 602 includes an image display region 604 that visually presents an image 606 with pixels intensities representing scanned renal pelvis calyces 620. The display region 602 further includes pictogram display region 608. In the illustrated embodiment, a 3D pictogram 610 is visually presented in the pictogram display region 608. The 3D pictogram 610 includes a 3D representation of kidneys 622, ureters 612, liver 614, vessels 616, etc., showing only certain organs and vessels. Graphical indicia 618 shows a location and orientation of the transducer array during data acquisition.

Figure 7:
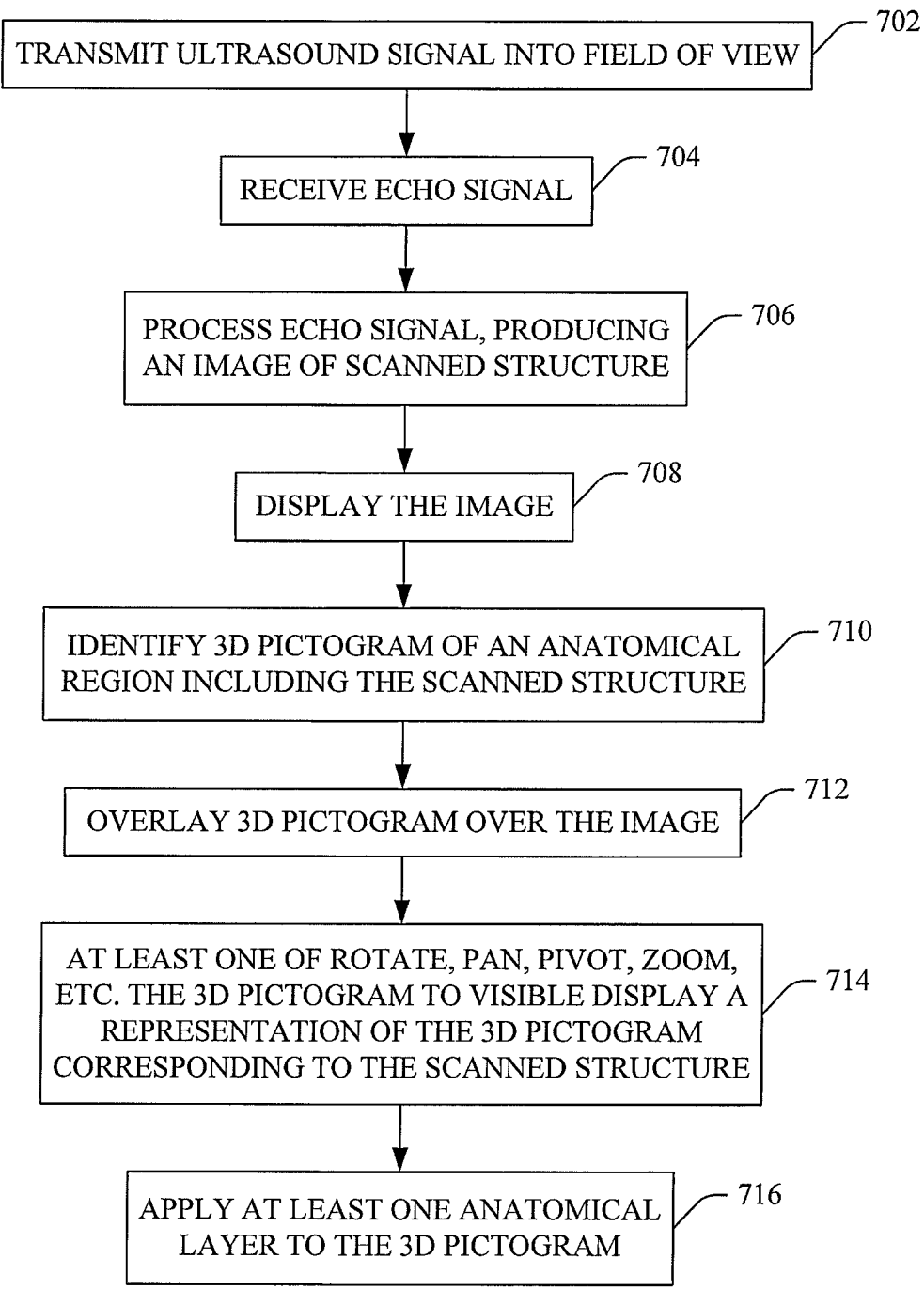
FIG. 7 illustrates an example method in accordance with the embodiments disclosed herein.

FIG. 7 illustrates a method in accordance with the embodiments disclosed herein.

It is to be appreciated that the order of the following acts is provided for explanatory purposes and is not limiting. As such, one or more of the following acts may occur in a different order. Furthermore, one or more of the following acts may be omitted and/or one or more additional acts may be added.

At 702, an ultrasound signal is transmitted into a field of view.

At 704, an echo signal, generated in response to the ultrasound signal interacting with structure in the field of view, is received.

At 706, the echo signal is processed, producing an image of the structure.

At 708, the image is visually displayed.

At 710, a 3D pictogram of an anatomical region including the structure is identified from a plurality of 3D pictograms.

At 712, the 3D pictogram is overlaid over the image.

At 714, the displayed 3D pictogram is at least one of rotated, panned, pivoted, or zoomed so that a representation of 3D pictogram corresponding to the structure is visible in the image.

At 716, at least one anatomical layer, such as a skin, a muscle, a bone, a vessel, etc. layer, is applied to the 3D pictogram.

The above methods may be implemented by way of computer readable instructions, encoded or embedded on computer readable storage medium, which, when executed by a computer processor(s), cause the processor(s) to carry out the described acts. Additionally or alternatively, at least one of the computer readable instructions is carried by a signal, carrier wave or other transitory medium.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. An ultrasound imaging system, comprising:
   a transducer array with at least one transducer element;
   an echo processor that processes ultrasound echo signals received by the at least one transducer element, producing an image of scanned tissue of interest;
   memory that stores a plurality of 3D pictograms, each representing different anatomical regions of a subject;
   a pictogram processor that identifies a 3D pictogram of the plurality of 3D pictograms corresponding to the scanned tissue of interest, wherein the 3D pictogram includes a 3D pictorial representation of an anatomical region including the scanned tissue of interest and includes a plurality of individually selectable anatomical layers including an organ layer, a muscle layer, a bone layer, and a vessel layer;
   a display monitor; and
   a rendering engine that displays the image and the 3D pictogram via the display monitor, wherein the 3D pictogram is overlaid over a pictogram region of the displayed image,
   wherein the pictogram processor includes a 3D pictogram manipulator that at least one of selectively adds or removes one or more of the plurality of individually selectable anatomical layers to or from the displayed 3D pictogram in response to a first signal indicative of a first input indicating the one or more anatomical layers of interest.

2. The ultrasound imaging system of claim 1, wherein the 3D pictogram manipulator rotates the displayed 3D pictogram until a pictorial representation of the scanned tissue of interest of the 3D pictogram is visible in the displayed image, wherein the pictorial representation of the scanned tissue of interest is not initially visible in the displayed 3D pictogram.

3. The ultrasound imaging system of claim 1, wherein the 3D pictogram manipulator identifies at least one of a plurality of anatomical layers, but not all of the plurality of anatomical layers, to visually show in the 3D pictogram.

4. The ultrasound imaging system of claim 1, wherein the 3D pictogram manipulator changes the at least one of the plurality of the displayed anatomical layers in response to a second signal indicative of a second input indicating a second different layer of interest.

5. The ultrasound imaging system of claim 1, the pictogram processor, comprising:
   a 3D pictogram annotator that overlays graphical indicia, which identifies a location and an orientation of the transducer array on the anatomical region during data acquisition, on top of the anatomical region in the displayed 3D pictogram at the location and showing the orientation.

6. The ultrasound imaging system of claim 5, wherein the 3D pictogram annotator overlays the graphical indicia in response to a graphical indicia signal indicative of a, input indicating the location and the orientation of the transducer array with respect to the 3D pictogram.

7. The ultrasound imaging system of claim 1, further comprising:
   an image processor that stores the 3D pictogram as part of the image.

8. A method, comprising:
   superimposing a 3D body mark of a plurality of 3D body marks over a 3D body mark region of a display region, wherein the display region concurrently displays an ultrasound image of scanned tissue of interest in an image display region of the display region, and wherein the 3D body mark includes a region of the body including the scanned tissue of interest; and
   visually presenting only a sub-set of a plurality of anatomical layers for the 3D body mark in the displayed 3D body mark, wherein the plurality of anatomical layers includes a bone layer, an organ layer, a muscle layer, and a vessel layer.

9. The method of claim 8, further, comprising:
   at least one of rotating, panning, zooming, or pivoting the 3D body mark displayed in the 3D body mark region to visibly display a graphical representation of the scanned tissue of interest.

10. The method of claim 8, further, comprising:
    filtering the plurality of the plurality of 3D body marks based on the scanned tissue of interest, thereby generating the sub-set of a plurality of 3D body marks corresponding to the scanned tissue of interest.

11. The method of claim 10, further, comprising:
    identifying a 3D body mark in the sub-set of plurality of 3D body marks in response to an input; and
    superimposing the identified 3D body mark.

12. The method of claim 11, further, comprising:
    obtaining an identification of the scanned tissue of interest from the image;
    identifying the 3D body mark in the sub-set of plurality of 3D body marks based on the obtained identification; and
    superimposing the identified 3D body mark.

13. The method of claim 8, further, comprising:
    receiving a location and an orientation for graphical indicia representing a transducer array used for data acquisition; and
    overlaying the graphical indicia over the displayed 3D body mark at the location, which visually identifies the location and the orientation of the transducer array with respect to the 3D body mark.

14. The method of claim 8, further comprising:
storing the 3D body mark with the image.

15. A non-transitory computer readable storage medium encoded with one or more computer executable instructions, which, when executed by a processor of a computing system, causes the processor to:
- transmit an ultrasound signal into a field of view;
- receive an echo signal generated in response to the ultrasound signal interacting with structure in the field of view;
- process the echo signal, generating an ultrasound image;
- display the ultrasound image of the structure;
- identify a 3D pictogram pictorially representing the structure in the image;
- superimpose the 3D pictogram over the ultrasound image; and
- visually present only a sub-set of a plurality of anatomical layers of the 3D pictogram in the displayed 3D pictogram, wherein the plurality of anatomical layers includes a bone layer, an organ layer, a muscle layer, and a vessel layer.

\* \* \* \* \*